(12) United States Patent
Pelz

(10) Patent No.: US 6,860,139 B2
(45) Date of Patent: Mar. 1, 2005

(54) APPARATUS FOR MEASURING GREEN-SPEED

(76) Inventor: David T. Pelz, 1310 Ranch Rd. 620, South, Suite B-1, Austin, TX (US) 78734

( * ) Notice: Subject to any disclaimer, the term of this patent is extended or adjusted under 35 U.S.C. 154(b) by 289 days.

(21) Appl. No.: 10/161,592

(22) Filed: Jun. 5, 2002

(65) Prior Publication Data
US 2003/0226393 A1 Dec. 11, 2003

(51) Int. Cl.[7] ............................................. G01N 19/02
(52) U.S. Cl. ............................................................ 73/9
(58) Field of Search ................................................ 73/9

(56) References Cited

U.S. PATENT DOCUMENTS 3,215,436 A * 11/1965 Carter ........................ 473/171
3,802,895 A * 4/1974 Dahlgren et al. ......... 106/166.42

* cited by examiner

Primary Examiner—Robert Raevis
(74) Attorney, Agent, or Firm—Welsh & Flaxman LLC

(57) ABSTRACT

Method and apparatus for measuring the green-speed of a putting green including a golf ball rolling ramp. The ramp is supported by adjustable length legs above a green surface at a selected angle. A level vial attached to the apparatus is used to determine when the ramp is at the selected angle. A plurality of parallel grooves extend the entire length of the rolling ramp and allow for sequentially rolling a plurality of golf balls onto a putting green surface. Located at the upper end of each groove is a trigger mechanism for each of said grooves, including a trigger support block and a trigger arm pivotally movable thereon for releasing the golf balls into the grooves and down the ramp. The forward or release end of the ramp is curved for releasing the balls parallel to the local horizontal relative to the putting green surface.

21 Claims, 5 Drawing Sheets

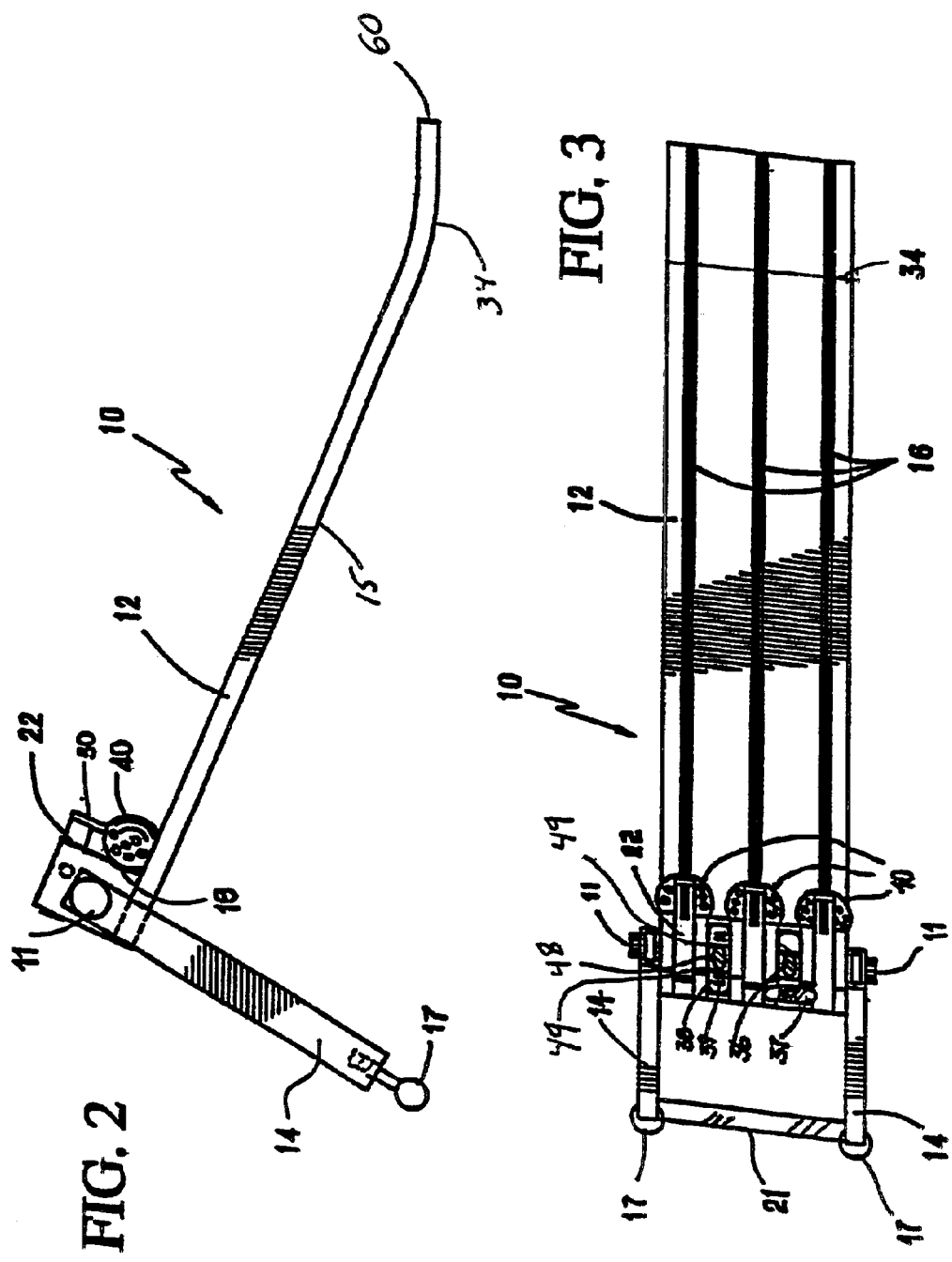

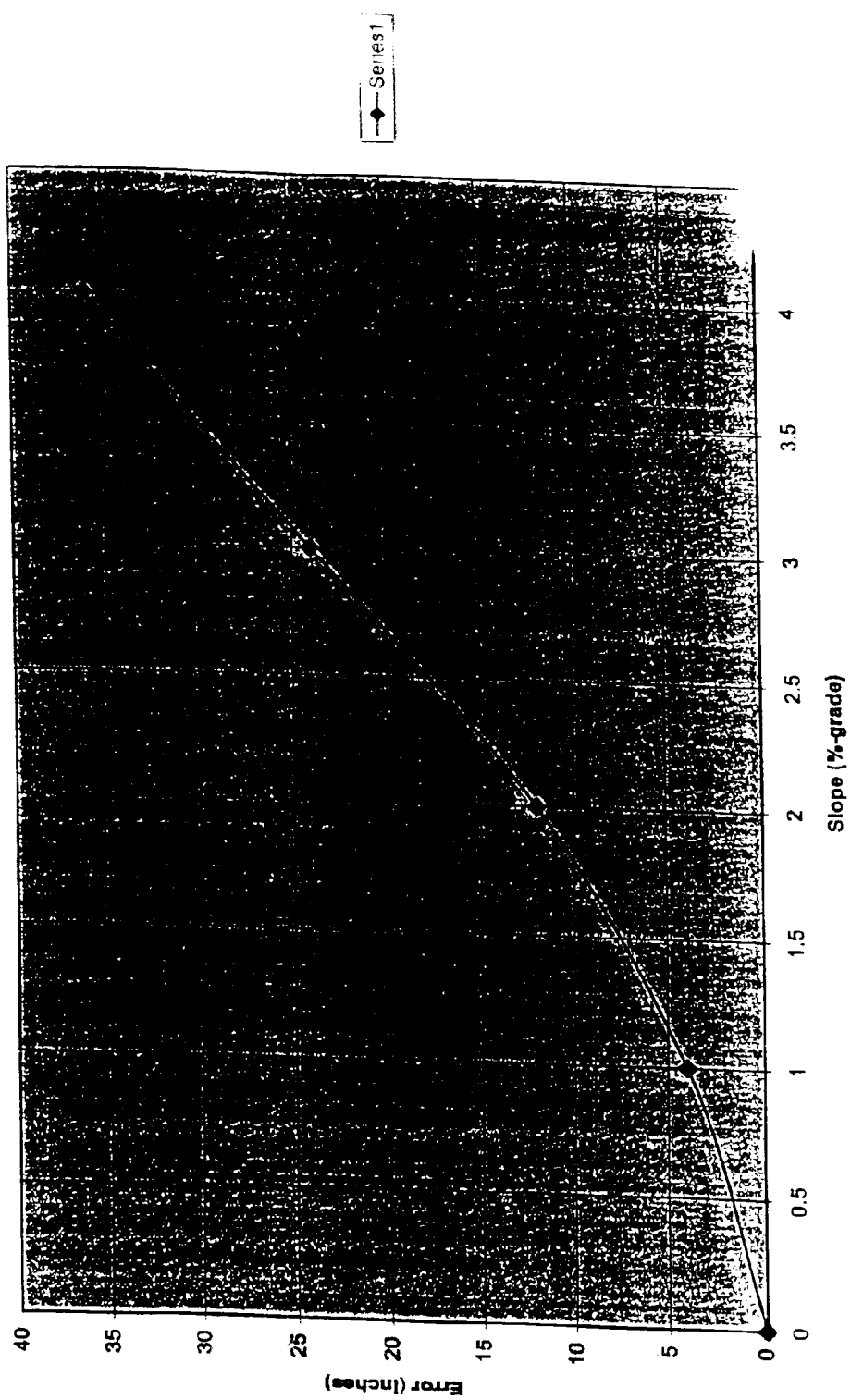

APPARATUS FOR MEASURING GREEN-SPEED

BACKGROUND OF THE INVENTION

The present invention relates to a method and an apparatus for measuring the "green-speed" of golf course greens. Green-speed more precisely is a measure of distance. It is a quantitative measurement of a green surface characteristic (green-speed), which relates to how far a golf ball rolls after being given a fixed initial speed (e.g. putted from an absolute reference stroke), and then using that quantity for green control, comparison and maintenance purposes. More particularly, the invention relates to an apparatus for measuring the green-speed of putting greens in a precise manner which improves on the current measuring practice.

The speed at which a golf ball rolls across a putting green toward the hole varies from golf course to golf course and sometimes from putting green to putting green on the same golf course. The faster the green-speed, the more skill is required to consistently hole putts in the least number of strokes. Golf course greens which have variations in green-speed between different greens or even differences in green-speed on the same green, require extraordinary skill on the part of the golfer to hole putts and usually result in considerably higher scores.

Ideally all golf greens on the same course are uniform with little variation in green-speed from one green to the next. Variances in green-speeds usually depend upon a wide variety of factors including maintenance procedures, grass types, weather conditions, number of rounds of golf played on the golf course and the skill level of golfers using the golf course, among others. For example, public golf courses with a large number of rounds and with a relatively large number of limited skill players tend to have green-speeds which are slow (between 6–8). Most upscale public golf courses and private golf clubs have greens with somewhat faster green-speeds (between 8.5–10). Courses which are used for tournament play, particularly professional tournaments, have green-speeds which are considerably faster (between 10.5–14).

Since 1976, in order to aid golf course superintendents to keep green-speeds consistent, and/or to regulate the green-speed for a particular event or playing condition, the green-speed of greens traditionally has been measured using a standard device called a Stimpmeter. This device was developed by Edward Stimpson to provide a standard device to consistently release a number of golf balls, one at a time, at a constant initial energy onto a green, to allow quantitative measurement of green-speed. The Stimpmeter is designed to be used on a wide variety of courses and for a wide variety of green conditions.

The Stimpmeter is a thirty-six inch long, straight aluminum bar with a V-shaped channel along its length, with a milled notch adjacent the upper portion of the V-shaped channel to accommodate a golf ball. The lower end of the Stimpmeter is provided with a beveled edge, which engages the surface of the green. In use, the beveled end of the Stimpmeter is placed on the green surface and a golf ball is placed in the notch. The Stimpmeter is designed so that a golf ball will be released and start to roll down the V-shaped channel when the notch end of the Stimpmeter is raised, by hand, to an angle of approximately 20 degrees, and then held absolutely still once the ball starts to roll down the ramp.

The United States Golf Association (USGA) specifies that to measure green-speed, three balls are sequentially rolled from a Stimpmeter over a relatively flat part of a green, in a first direction and the average roll distance measured. The test is repeated with the balls rolling over the same area, in the opposite direction. The average distance of all six rolls then represents the green-speed. This USGA specified Stimpmeter measurement has been the standard for many years and is recognized, not only by golf course superintendents, but also by the various local, national and international golf associations.

The design of the Stimpmeter often produces a number of inaccuracies in green-speed measurement. The release height of a golf ball placed in the notch in the V-shaped channel depends upon the dimple configuration and exact placement position of the golf ball relative to the edge of the notch. This causes errors in the initial speed of release of balls onto the green surface, which in turn, cause direct errors in green-speed measurements. Operator error, such as lifting or raising the bar in a jerky motion or not holding the bar steady as the ball rolls during a test may also cause a relatively large variation in roll distance. The flat sides of the V-shaped channel often causes golf balls rolling on dimple flats to chatter and bounce against the sides of the channel, which also affects roll distance. Because balls impact the green surface at the lower end of the Stimpmeter at a 20 degree angle, they bounce, thereby creating further variables in roll distance. Three balls are used, each rolled from the same spot in the same direction, and frequently a ball roll track is formed in the grass on the green, causing roll distances to be erroneously longer with each successive ball rolled in a previous ball track. Still further, the Stimpmeter is unable to detect slopes in the surface of the greens to be measured.

The prior art, other than the Stimpmeter, is mostly silent with respect to devices for reading green-speed.

U.S. Pat. No. 3,215,436 to Carter, directed to a green surface, shows a green-speed measuring device with a V-shaped ball channel supported at an angle of 30 degrees on a tripod support. The lower end of the track is formed with curved extensions tapering to a point. A golf ball is released down the channel. The distance the ball rolls is used to create a coefficient of putting friction which represents the green-speed of the putting surface.

U.S. Pat. No. 5,358,446 to Bergman shows a ramp used to roll a bowling ball with a lower forward rail portion which is horizontal to the alley surface.

SUMMARY OF THE INVENTION

The green-speed measuring apparatus of the present invention represents an improvement over the conventional Stimpmeter, green-speed measuring device. The present invention provides a green-speed reading apparatus which provides more accurate and consistent readings with less errors.

The green-speed measuring apparatus includes a three track ramp for rolling three golf balls along parallel, but distinct tracks over the surface of a green being tested. The ramp is raised above the putting surface to a precise 20.2 degree angle relative to the local horizontal using a preconfigured angled level-vial and an adjustable-length leg structure which mechanically supports the upper start end of the ramp at a fixed position. The local horizontal is defined as a plane perpendicular to the local gravitational vertical vector. Each golf ball sits in a radiused rolling groove against a radiused ball stop and is held in a pre-release starting position by a release trigger holding plate, which is also radiused to hold golf balls in a repeatable position, regardless of ball surface dimple location or size. The ramp has three ball-radiused rolling grooves which reduce golf ball chatter when a dimpled surface ball rolls down the grooves. The end of the ramp is curved in order to release golf balls horizontally so as to be essentially parallel to the putting green surface thereby minimizing or totally eliminating ball bounce as the ball impacts the surface of the green.

Other features of the apparatus include a level-vial to accurately determine the 20.2 degree release angle, relative to the local horizontal, to give all balls the same initial energy and speed. A flat bottom surface which works with second and third level-vials to determine side-to-side slope (cross slopes) and front to rear slope (fall line slopes). The legs are folded to a closed, non-use position, to enable the flat bottom of the device in conjunction with the second and third level-vials to read both the precise direction of the green surface slope fall-line, and its slope value in percentage of grade to ensure that the slope of the green surface is within viable parameters before a test is made. The release trigger has a holding plate to accurately and consistently grip a golf ball in the same starting position height, regardless of surface dimple size or location prior to each test. The release trigger also includes a release trigger window, which is used to precisely position a golf ball, marked for its balanced line, to further insure a consistent, true roll during the test.

Among the objects of the present invention is the provision of a green-speed measuring apparatus which represents an improvement of the conventional Stimpmeter green-speed measuring device.

Another object of the present invention is the provision of a green reading method and apparatus which provides more accurate and consistent readings of green-speed.

Still another object of the present invention is the provision of a green-speed measuring method and apparatus which provides a roll ramp which is precisely located at the same release angle relative to the local horizontal each time a golf ball is used to test the green-speed of a golf green.

Another object of the present invention is the provision of a green-speed measuring method and apparatus which has three independent rolling grooves resulting in three different and parallel ball tracks on the putting surface.

An additional object of the present invention is the provision of a green-speed measuring method and apparatus which has a rolling ramp with a curved lower surface, which releases a golf ball horizontal onto a putting green surface, in order to minimize or eliminate ball bounce when the test balls are released.

Still another object of the present invention is the provision of a green-speed measuring method and apparatus, which has a precise ball release mechanism to promote more consistent rolls for more accurate results.

Yet another object of the present invention is to provide ball-radiused tracks in the ramp to aid in reducing ball chatter.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a front elevational view thereof.

FIG. 3 is a top plan view thereof.

FIG. 7 is a graph showing Green-speed error vs. Slope used to determine error correction in inches.

DESCRIPTION OF THE PREFERRED EMBODIMENTS

Figure 1:
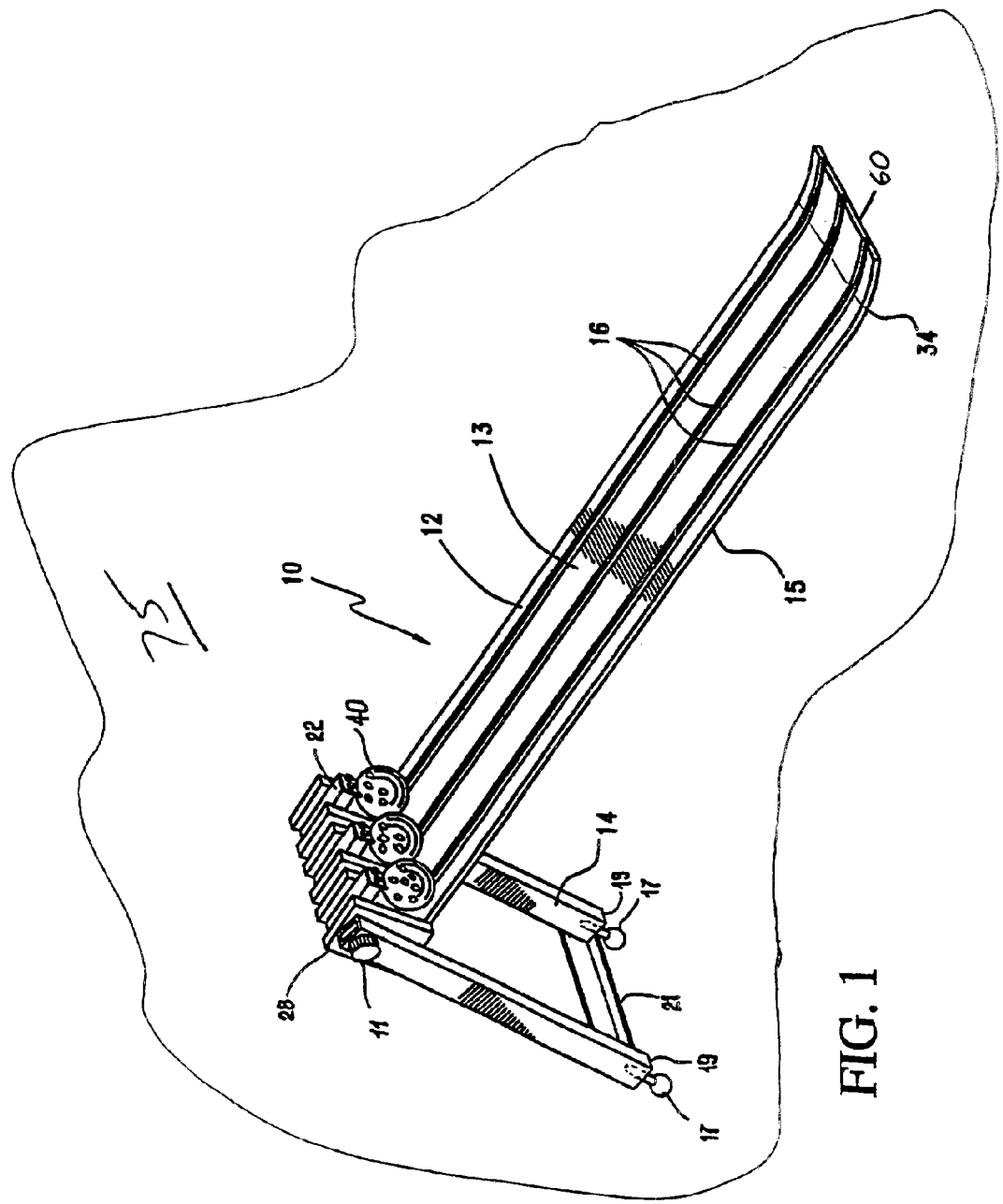
FIG. 1 is a perspective view of the green-speed reading apparatus of the present invention.

The detailed embodiments of the present invention are disclosed herein. It should be understood, however, that the disclosed embodiments are merely exemplary of the invention, which maybe embodied in various forms. Therefore, the details disclosed herein are not to be interpreted as limited, but merely as the basis for the claims and as a basis for teaching one skilled in the art how to make and/or use the invention.

Referring to the drawings, the green-speed reading apparatus 10 of the present invention is formed of a golf ball rolling ramp 12 supported above a green surface 75 at an angle of 20.2 degrees in the test position with a pair of spaced legs 14. The legs 14 are spaced by a cross bar 21 and are pivotally and removably secured to the ramp 12 by threaded knobs 11. Legs 14 pivot when knob 11 is loosened such that the legs are folded onto the top side of the ramp 12 for storage and when the apparatus is used as a site selection aid. When the legs 14 are folded over and cross bar 21 rests on the upper surface of ramp 12, a device with a flat bottom surface is created which allows the flat surface of the apparatus to be used for measuring putting green slopes as described hereinbelow. The legs 14 include castors 17 which are screwed into the bottom 19 of legs 14 and are adjustable so the overall length of the legs 14 may be varied to accommodate variations or imperfections in the surface of a putting green being measured.

The ramp 12 is formed with three parallel, golf ball rolling tracks in the form of grooves 16 extending the entire length of the ramp 12. These grooves are milled with a radius compatible with the outside dimensions of a golf ball and present a smooth rolling surface to dimpled golf balls having a standard 1.68 inch diameter. This structure reduces chatter and allows the ball to roll true, as opposed to bouncing on the dimples of the ball, as the golf ball rolls down the groove 16 toward the green surface. If the grooves were V-shaped the balls would chatter as they bounced when the dimples contacted the edges of the V-shaped groove. Because three separate rolling grooves 16 are provided, the golf balls roll on three distinctly different parts of the putting green surface and produce three separate, distinctly different ball tracks which eliminate the inconsistencies in rolling distance when three balls roll along the same track.

Figures 4, 5:
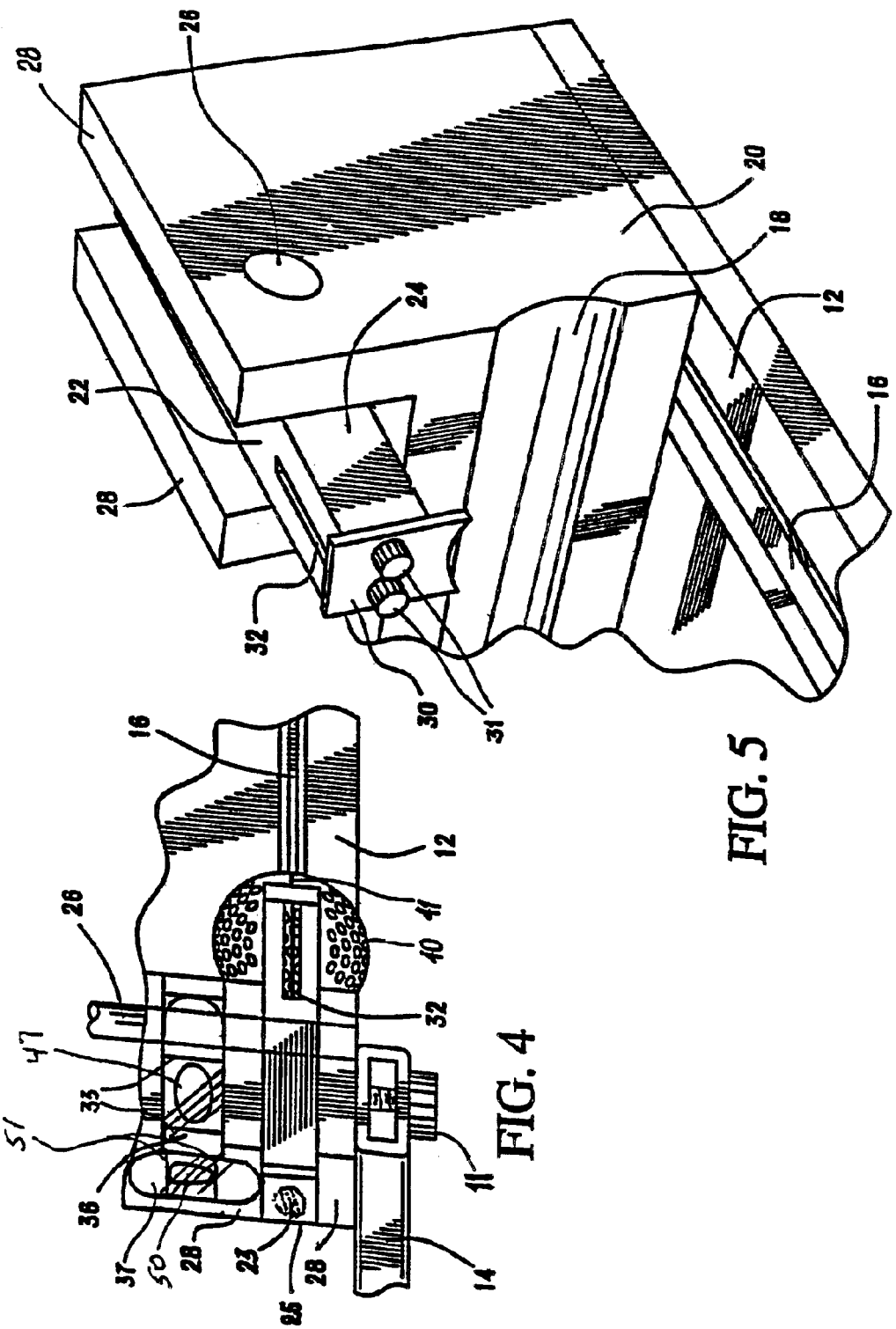
FIG. 4 is a view of a detail of the apparatus of the present invention.
FIG. 5 is a view of another detail of the apparatus of the present invention.

In the test position, each golf ball 40 sits in one of the radiused rolling grooves 16 and rests against a radiused back stop 18 on the trigger support block 20. A trigger mechanism 22 is formed of a trigger arm 24 mounted on a pivot rod 26 pivotally movable on upright supports 28 of the trigger support block 20. The end of the trigger mechanism 22 is formed with an arcuate ball holder 30 connected to the end of the trigger arm 24 via bolts 31. The arcuate ball holder 30 is contoured to contact the exact top of a golf ball 40 when it is properly seated in the groove 16 and against the radiused back stop 18. The arcuate ball holder 30 of the trigger arm 24 is biased against the golf ball 40 by a resilient spring or sponge-like material 23 shown in dotted lines in FIG. 4 placed on the support block 20 at the rear end 25 of trigger arm 24. Therefore, when rear end 25 is depressed against resilient material 23 the front end of trigger arm 24 will raise and the golf ball begins to roll down the ramp.

Each trigger arm 24 has a slotted window 32 which enables the tester to repeatedly align golf balls 40 marked with a circumferential balance line 41 to further insure consistency when the golf balls 40 roll along the green surface.

The lower, forward or release end 60 of the ramp 12 is curved beginning just after slope-line 34 so as to lie horizontal and parallel to the local horizontal and the putting green surface when the apparatus 10 is in the test position. The curved forward end (i.e. from 34 to 60) of the ramp 12 releases the golf balls horizontally to the putting surface thereby eliminating or minimizing bounce as the balls impact the putting green surface.

Three level-vials 36, 37 and 38 are mounted on the trigger support block 20. The first level-vial 36 is preconfigured at an angle of 20.2 degrees relative to the horizontal. Thus, when bubble 47 is located between window lines 33, the angle of the ramp 12 relative to the local horizontal is known to be at 20.2 degrees.

The second level-vial 37 assists in determining if cross slopes exist when the apparatus is placed at a selected site. When green-speed testing begins it is desirable to select a site with no cross slope and as little fall line slope as possible. Thus, the flat bottom surface 15 of the ramp is placed on the selected putting green site and slid around until the bubble 50 is located between window lines 51 in the second level 37.

The third level-vial 38 is used in combination with the flat bottom surface of the green reading apparatus 10 to determine if a particular surface on a putting green is suitable for a test or to correct for slope error. Level-vial 38 measures the precise direction of the surface fall line slope and the magnitude of the surface slope. If the bubble 48 in the level-vial 38 stays within the marked lines 49, the site is suitable for an accurate test of green-speed. Second level-vial 37 is located at a right angle relative to level-vial 38. The window on level-vial 38 includes addition lines 39 which function to indicate a percent slope grade. The first line indicates a 1% slope grade, the second line indicates a 2% slope grade, a third line (not shown) indicates a 3% slope grade and a fourth line (not shown) indicating a 4% slope grade. As such, the location of the bubble 48 can be used to quickly ascertain the slope grade. That is, depending on which line the bubble contacts a user can visually determine percent slope. The percent slope number can then be compared to the graph shown in FIG. 7 to determine a correction error in inches. For example, if the percent slope is determined to be 3, the error correction number would be 24 inches. The 24 inches would then be subtracted from the distance each ball rolled during testing from that selected site to correct for the large slope which caused the ball to roll farther. The plotted line in FIG. 7 was determined by repeated experimental testing on grades of varying slope.

Figure 6:
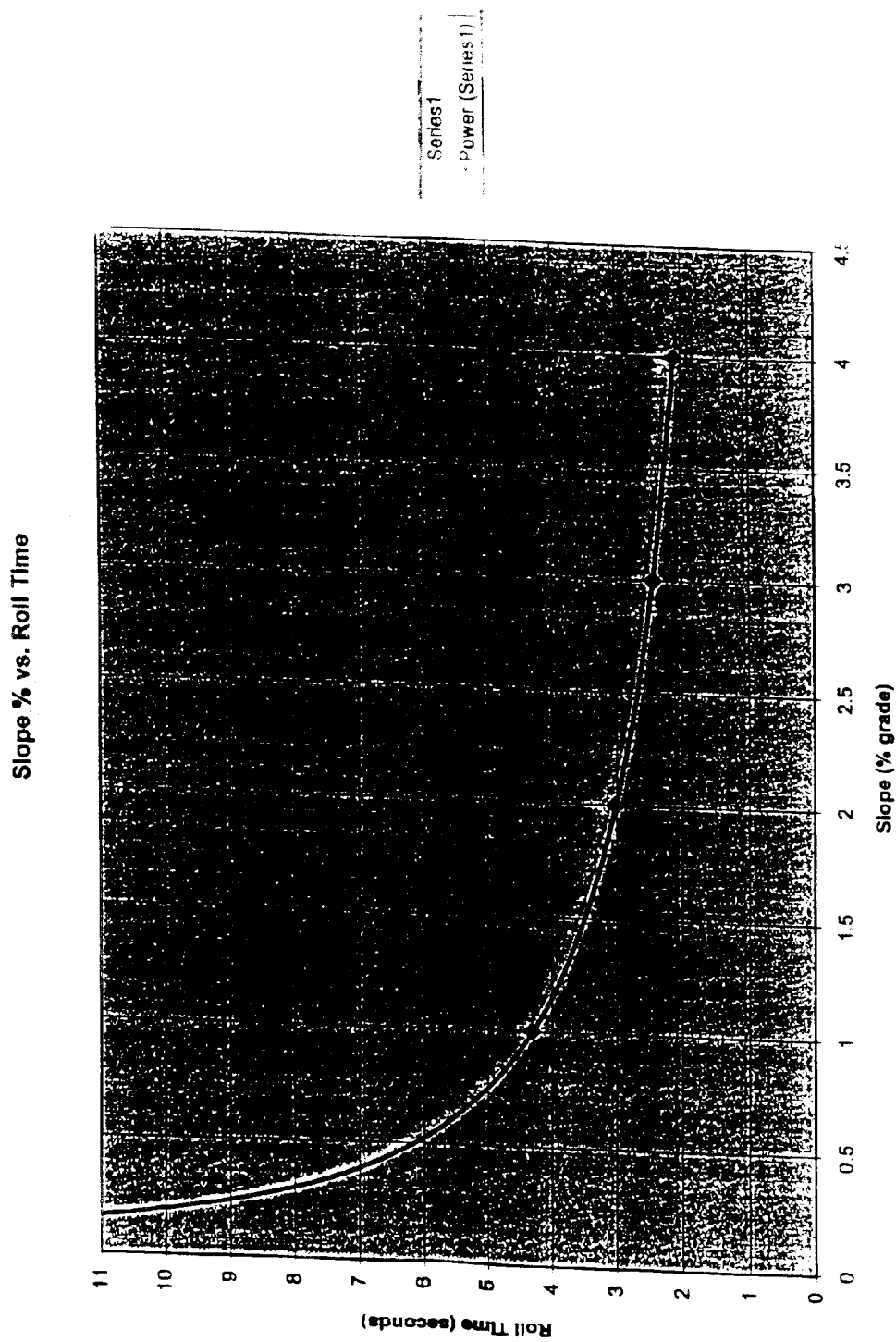
FIG. 6 is a graph showing Slope % vs. Roll Time used to determine slope.

Additionally the percent slope grade can be determined by the roll time of the ball on the ramp when the apparatus is laying flat on the selected site. The time it takes for a ball to roll the predetermined "slope-determining distance" (from a position just touching the outside of a release trigger near one end of the ramp, to the slope-line 34 which is marked on the ramp just short of where the ramp starts to curve at its other end, or vice-versa) is measured, the fall-line percent slope grade of the green is determined from the "Slope vs. Roll Time" curve plotted on the graph shown in FIG. 6. The line plotted in FIG. 6 was obtained by repeated experimental testing on slopes of varying percent slope grade. The percent slope grade is then compared with the graph in FIG. 7 to obtain an error correction factor as discussed above.

In use, a site on a putting green is selected by observing and determining what appears to be the most level area on the putting green to be tested. The flat bottom 15 of the apparatus 10 is set on the putting green and moved around reading level-vials 37 and 38 to assist in selecting a site on the putting a green which is relatively flat. As discussed above when bubble 50 of level-vial 37 is located between window lines 51 no cross slopes exist and this is a desirable location. When bubble 48 of level-vial 38 is located between window lines 49 this is a desirable location. However, it is quite common for a putting green surface to have a fall line slope and as such the slope and error correction factor must be determined as discussed above.

Once the site is selected and the fall line percent grade slope determine, legs 14 of the apparatus 10 are pivoted into an upright position and locked into place by tightening knobs 11. The height of legs 14 are then adjusted by threading in or out adjustable caster feet 17 until bubble 48 within level-vial 38 reads level, that is the bubble is located within the marked window lines 49. At this position testing can now begin as the ramp 12 is angled at 20.2 degrees relative to the local horizontal and accurate distance readings can be obtained as each of the balls when released should theoretically roll down the ramp at the same speed under the force of gravity.

Three golf balls are placed in the start position in each of the grooves 16 and against the radiused back stop 18. The trigger arm 24 is gently raised against the pressure of the resilient material 23 and the arcuate ball holder 30 is allowed to contact the top surface of each ball 40 to hold the ball in place. Each ball may include a balanced line 41 which is aligned within window 32 by simply rotating the golf ball to a proper position once the golf ball 40 is retained by trigger arm 24 and arcuate ball holder 30. When a test is conducted, the rear end 25 of all three trigger arms 24 are sequentially pressed causing its associated arcuate ball holder 30 to raise and release a golf ball allowing it to roll down a groove 16 on the ramp 12 and onto the green surface in response to the natural effects of gravity. The distance each ball rolls is measured from the slope-line 34 to the spot at which the ball came to rest. The test is repeated with the green reading apparatus facing in an opposite direction, rolling the three balls over the same area of the green surface. The average of all the distances the balls roll is calculated to determine the green-speed of the green and then adjustments are made for fall line slope and an accurate green-speed distance is recorded and the selected site noted for future tests.

While various preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A method of determining the green-speed of a golf putting green comprising:

selecting a site on a putting green having a relatively flat surface;

setting a green-speed reading apparatus including a rump having a raised start end and a ground contacting release end with a plurality of parallel, golf ball rolling tracks thereon, in a first direction whereby the release end of the ramp contacts the putting green surface at said selected site;

placing and retaining at start positions a golf ball in each of said plurality of parallel golf ball rolling tracks, said start positions are at the raised start end of said tracks;

releasing said plurality of golf balls from the start positions, allowing the balls to roll down said plurality of parallel track, by gravity onto the putting green surface;

measuring the distance each ball rolls across the putting green from a slope line marked on the ramp;

repeating the test with said apparatus facing in the opposite direction at said selected site and measuring the distance each ball rolls across the putting green from a slope line marked on the ramp; and calculating the average distance of all the golf balls rolled to determine a value in terms of green-speed.

2. The method of claim 1 wherein the retaining step is further defined by holding the balls at each start position with a trigger arm; and, the releasing step is further defined by raising the trigger arm to release the balls.

3. The method of claim 1 wherein the site selecting step is further defined by the step of identifying a site without any cross slopes via the use of a level and at this site determining the pure downhill, fall line direction and measuring the percent slope grade of the green surface relative to the local horizontal at the selected site.

4. The method of claim 3 wherein measuring the percent slope grade of the green surface is accomplished by timing the roll of a ball from the start end of the ramp to the slope line marked on the ramp.

5. The method of claim 1 further including the step of adjusting and mechanically maintaining the height of the start end of said ramp such that the ramp is at a predetermined angle relative to the local horizontal with said release end of ramp contacting the putting green surface at said selected site.

6. The method of claim 5 wherein said predetermined angle is 20.2 degrees.

7. The method of claim 1 wherein the releasing step is performed sequentially.

8. The method of claim 4 wherein the green-speed is adjusted by an error correction factor if the percent slope grade is greater than zero.

9. The method of claim 8 wherein the error correction factor is determined by Brede's formula.

10. An apparatus for measuring the green-speed of a putting green comprising:

a golf ball rolling ramp supported above a putting green surface at a selected site and at a selected angle relative to the local horizontal;

a plurality of parallel golf ball rolling tracks in the form of grooves extending the entire length of the rolling ramp;

legs attached to the ball rolling ramp for supporting said ramp at the selected angle;

a trigger mechanism for each of said tracks for holding the golf balls in the grooves and releasing the golf balls when activated down said ramp and onto the putting green surface.

11. The apparatus of claim 10 wherein said legs are adjustable in length and pivotally attached to said ramp so as to be foldable thereagainst.

12. The apparatus of claim 10 wherein said grooves are radiused to the diameter size of a standard golf ball.

13. The apparatus of claim 10 wherein said trigger mechanism includes a trigger arm pivotally mounted on a trigger support block and having an arcuate ball holder for holding a golf bail in the same position each time it is placed on the support block.

14. The apparatus of claim 13 further including a back stop on said trigger support block radiused to the diameter size of a standard golf ball, for holding a golf ball in a fixed position relative to said trigger arm.

15. The apparatus of claim 10 further including a first level-vial preconfigured on the ramp at said selected angle relative to the local horizontal.

16. The apparatus of claim 15 wherein said selected angle relative to the local horizontal is approximately 20 degrees.

17. The apparatus of claim 15 further including a second level-vial for determining if cross slopes exist when the apparatus is placed at the selected site.

18. The apparatus of claim 17 further including a third level-vial for locating the pure downhill, fall line direction at any position on the putting green surface and as a means for measuring the percent slope grade of the putting green surface.

19. The apparatus of claim 10 further including an alignment slot in said trigger mechanism to enable a user to see and properly align a golf ball marked with a balanced line in the trigger mechanism.

20. The apparatus of claim 10 wherein said ramp includes a curved release end which lies parallel to the putting green surface at the point of golf ball release.

21. An apparatus for measuring the green-speed of a putting green comprising:

a golf ball rolling ramp supported above a green surface at a selected angle;

legs attached to the rolling ramp for supporting said ramp and adjusting the ramp to a selected angular position, said legs being adjustable in length and pivotally attached so as to be foldable against said ramp;

a plurality of parallel grooves radiused to the diameter size of a standard golf ball, extending the entire length of the rolling ramp;

a trigger mechanism for each of said grooves;

said ramp including a curved forward end lying parallel to the green surface for releasing the balls onto the green surface; and a plurality of level vials for measuring angles relative to the local horizontal and the level of the green itself.

* * * * *